United States Patent [19]

Mita et al.

[11] 4,453,008
[45] Jun. 5, 1984

[54] PRODUCTION PROCESS OF DL-CYSTEIN

[75] Inventors: Ryuichi Mita, Kawasaki; Masaharu Ohoka, Yokohama; Chojiro Higuchi, Kamakura; Toshio Katoh, Kawasaki; Nobuyuki Kawashima; Akihiro Yamaguchi, both of Kamakura; Shousuke Nagai, Yokohama; Takao Takano, Fujisawa, all of Japan

[73] Assignee: Mitsui Toatsu Chemicals, Inc., Tokyo, Japan

[21] Appl. No.: 459,533

[22] PCT Filed: May 26, 1982

[86] PCT No.: PCT/JP82/00198

§ 371 Date: Jan. 14, 1983

§ 102(e) Date: Jan. 18, 1983

[87] PCT Pub. No.: WO82/04251

PCT Pub. Date: Dec. 9, 1982

[30] Foreign Application Priority Data

Jun. 1, 1981 [JP] Japan .................................. 56-82453

[51] Int. Cl.³ .......................................... C07C 149/247
[52] U.S. Cl. .................................. 562/557; 260/455 B

[58] Field of Search ..................... 562/557, 558, 556; 260/455 B

[56] References Cited

U.S. PATENT DOCUMENTS

| 2,710,304 | 6/1955 | Opfermann | 562/557 |
| 3,646,094 | 2/1972 | Brooks | 260/455 B |
| 3,897,480 | 7/1975 | Mita | 260/455 B |

FOREIGN PATENT DOCUMENTS 1023003 3/1966 United Kingdom ............... 562/556

Primary Examiner—Michael L. Shippen
Attorney, Agent, or Firm—Fisher, Christen & Sabol

[57] ABSTRACT

DL-cystein is produced by reacting a β-halogenoalanine with a trithiocarbonate to obtain the mono(aminocarboxyethyl) ester of trithiocarbonate and then subjecting the ester to acid decomposition. The above process requires mild reaction conditions, is easy to carry out its reactions and can afford DL-cystein with high yield. It is thus an excellent production process of DL-cystein from the industrial viewpoint.

7 Claims, No Drawings

PRODUCTION PROCESS OF DL-CYSTEIN

DESCRIPTION

1. Technical Field

This invention relates to a novel process for producing cystein. More specifically, it relates to a process for producing DL-cystein by reacting a β-halogenoanaline with a trithiocarbonate and then decomposing the resulting mono(aminocarboxyethyl) ester of the trithiocarbonate with an acid.

2. Background Art

Cystein is a sulfur-containing amino acid and has found utility as a food additive and for the production of pharmaceutical products, cosmetic products and the like. Conventionally, it has been industrially produced by the electrolytic reduction of cystine extracted from naturally-occurring sources such as human hair.

A wide variety of processes have heretofore been proposed to achieve a chemical synthesis of cystein. Under the circumstances, they are generally accompanied by such drawbacks that they require long reaction steps and complex operations. In addition, they are not fully satisfactory with respect to their production yields. Among such processes, there have been known, as processes for producing cystein from a β-halogenoalanine, (1) to react β-chloroalanine with barium hydrosulfide [Ber., 41, 893 (1908)]; (2) to react β-chloroalanine with mercaptobenzyl to obtain β-benzylthioalanine and then reducing the resultant compound with sodium in liquid ammonium [J. Biol. Chem., 179, 529 (1949)]; and (3) to block the amino group and carboxyl group of β-chloroalanine with protecting groups and react the thusprotected compound with thioacetic acid, followed by its hydrolysis [Nippon Kagaku Zasshi, 89, 716 (1968)]. However, the above process (1) is liable to induce the by-production of sulfides, disulfides and the like which are difficult to remove and is thus accompanied by a shortcoming of poor yield. On the other hand, the above processes (2) and (3) each requires lengthy reaction steps and their operations are complex and cumbersome. Thus, their overall yields are considerably low and they have little industrial value. It has recently been proposed to first react β-chloroalanine with a thiosulfate to obtain S-sulfocystein and then subject it to hydrolysis under acidic conditions to produce cystein (Japanese Patent Laid-open No. 164669/1980). It seems to be difficult to expect high yield for cystein because the preparation step of S-sulfocystein is carried out under heated, refluxing conditions despite of the poor thermal stability of β-chloroalanine in the form of a solution.

INVENTION DISCLOSURE

An object of this invention is to provide a process for producing cystein with high yield.

Another object of this invention is to provide a process for producing cystein under mild reaction conditions through simple reaction operations.

According to this invention, there is thus provided a process for producing DL-cystein, which process comprises reacting a β-halogenoalanine with a trithiocarbonate and then subjecting the resulting mono(aminocarboxyethyl) ester of trithiocarbonate to acid decomposition.

BEST MODE FOR CARRYING OUT THE INVENTION

The process according to this invention comprises reacting a β-halogenoalanine with a trithiocarbonate to obtain the mono(aminocarboxyethyl) ester of the trithiocarbonate and then decomposing the resultant mono(aminocarboxyethyl) ester of the trithiocarbonate with an acid into cystein.

The starting material used in the process according to this invention, i.e., a β-halogenoalanine is an alanine derivative whose carbon atom at the β-position is substituted by a halogen atom. As such a β-halogenoalanine, may be metioned for example β-chloroalanine or β-bromoalanine. It may be readily produced by subjecting an azilidine-2-carboxylate to a ring-opening reaction with a hydrohalogenic acid such as hydrochloric acid or hydrobromic acid in an aqueous reaction medium or by converting its corresponding halogenoacetoaldehyde into its sulfite-addition product, then reacting it first with ammonia and then with hydrocyanic acid to obtain an α-amino-β-halogenopropionitrile, and finally subjecting the resultant α-amino-β-halogenopropionitrile to hydrolysis in a mineral acid.

As the trithiocarbonate usable in the present process, an alkali metal or alkaline earth metal salt or the ammonium salt of trithiocarbonic acid is generally mentioned. More specifically, lithium trithiocarbonate, sodium trithiocarbonate, potassium trithiocarbonate, potassium sodium trithiocarbonate, calcium trithiocarbonate, magnesium trithiocarbonate or ammonium trithiocarbonate may be mentioned. Among such trithiocarbonate, the alkali metal salts and ammonium salt of trithiocarbonic acid are preferred.

In the process according to this invention, the trithiocarbonate may be used in an amount range of 1–10 moles, and preferably 1–5 moles per mole of the β-halogenoalanine.

The reaction is generally carried out in an aqueous medium which may contain, without deleteriously affecting on the reaction, alcohols such as methanol, ethanol and isopropanol, organic solvents miscible with water such as dioxane, acetone and tetrahydrofuran, and organic solvents immiscible with water such as hydrocarbons led by benzene, toluene and xylene.

There is no special limitation to the order in which the raw materials are added. For example, the β-halogenoalanine may be added or dropped in a solid or slurry state or in the form of an aqueous solution to an aqueous solution of the trithiocarbonate. Alternatively, the β-halogenoalanine may in advance be suspended in water or converted into an aqueous alkaline solution and the trithiocarbonate may then be added in the form of an aqueous solution to the aqueous suspension or aqueous alkaline solution.

The reaction may be proceeded without encountering any problems even if an alkali such as sodium hydroxide, potassium hydroxide or ammonia is beforehand dissolved in the aqueous solution of the trithiocarbonate.

The reaction temperature between the β-halogenoalanine and trithiocarbonate ranges from −20° C. to +100° C., and preferably from 0° C. to 80° C., while the reaction time may be 1–30 hours, and preferably 2–20 hours.

The mono(aminocarboxyethyl) ester of the trithiocarbonate is formed as mentioned above. The end of the reaction can be readily determined using analytical means such as high-speed liquid chromatography.

According to the process of this invention, it is unnecessary to isolate the intermediate, i.e., the mono(aminocarboxyethyl) ester of the trithiocarbonate from the reaction system. Generally, the intermediate is readily decomposed into cystein by adding an acid into the reaction mixture or the reaction mixture into the acid and making the reaction mixture acidic without isolating the intermediate from the reaction mixture. There is no special limitation vested on the acid to be employed in this acid decomposition. Any acid may be used so far as it is an inorganic or organic acid. In view of the subsequent isolation of cystein and from the industrial standpoint, a mineral acid such as hydrochloric acid or sulfuric acid is normally used. Instead of using hydrochloric acid, hydrogen chloride gas may be blown into the reaction system.

No particular limitation is present to the conditions of this acid decomposition. It is usually carried out at 0°–80° C., and preferably 0°–50° C. for 0.5–5 hrs., and preferably 1–3 hours or so. Carbon disulfide, which is formed as a by-product by the acid decomposition, is recovered by distillation and reutilized for the production of the trithiocarbonate.

The present process may be effected in any atmosphere. The formation of cystine through the oxidation of cystein can be suppressed if both the first ester-forming reaction step and second acid decomposition step are carried out in the atmosphere of an inert gas.

In the present process, the final product DL-cystein can be isolated as free DL-cystein by a method known per se in the art, for example, by using isolation means such as an electrodialyzer, or by adding p-toluenesulfonic acid, p-chlorobenzenesulfonic acid or the like to the reaction liquid to separate DL-cystein as its crystalline salt, dissolving the salt in an alcohol and then neutralizing the alcoholic solution with an organic base such as ammonia or triethylamine. Alternatively, it may still be possible to isolate DL-cystein by removing the inorganic salt, which is present together with the DL-cystein in the reaction liquid, by a suitable method and then recrystallizing DL-cystein as the hydrochloric acid salt from hydrochloric acid.

Compared with the above-mentioned prior art processes, the present invention has such merits that it provides higher cystein yield, requires milder reaction conditions and simpler reaction operations and enjoys higher volumetric efficiency of the reaction. Thus, the process according to this invention has a high value from the industrial viewpoint.

The present process will hereinafter be described in the following examples.

EXAMPLE 1

While stirring at 15°–20° C. 60.8 g of a 38 wt. % aqueous solution of sodium trithiocarbonate, 12.35 g of β-chloroalanine was charged over 30 minutes. They were allowed to undergo a reaction at the same temperature for 5 hours. Thereafter, 31.2 g of 35% hydrochloric acid was gradually added while maintaining the reaction mixture at 15°–20° C., thereby making the resultant reaction liquid acidic. The reaction liquid was stirred at the same temperature for one hour. Carbon disulfide, which was by-produced through the acid decomposition, was recovered by distilling the reaction liquid (the amount of carbon disulfide recovered: 10.5 g). After removing carbon disulfide, the remaining reaction liquid was analyzed by high-speed liquid chromatography (column: Shodex OH Pak B-804; mobile phase: $8 \times 10^{-3}$ mole/liter aqueous $H_3PO_4$ solution; and measurement temperature: room temperature). The above analysis showed that the yield of DL-cystein was 80.5 mole % based on β-chloroalanine.

Subsequent to cooling the reaction liquid, 16.2 g of p-toluenesulfonic acid hydrate was added and agitated. The mixture was cooled to 5° C. or below and the resulting deposit of DL-cystein p-toluenesulfonate was collected through filtration and then washed with a small amount of cold water. It was then dried to give 21.4 g of DL-cystein p-toluenesulfonate.

The thus-obtained DL-cystein p-toluenesulfonate was dissolved in 200 ml of methanol and added with 7.4 g of triethylamine. It was then stirred, resulting in the formation of a DL-cystein deposit. The deposit gave 8.4 g of DL-cystein (yield: 69.4 mole % based on β-chloroalanine).

Elementary analysis (% by weight):

Calculated for $C_3H_6NO_2S$: C, 29.74; H, 5.82; N, 11.56; S, 26.46. Found: C, 29.52; H, 5.93; N: 11.35; S: 26.40.

EXAMPLE 2

While stirring at 5°–10° C. 64.3 g of a 58 wt. % aqueous solution of potassium trithiocarbonate in a gentle nitrogen gas flow, 12.35 g of β-chloroalanine was added thereto in the course of about one hour. It was allowed to undergo a reaction at the same temperature for further 5 hours. The resultant reaction mixture was then poured slowly into 41.7 g of 35% hydrochloric acid while maintaining the latter at 10°–20° C., followed by its further mixing at the same temperature for one hour. Carbon disulfide, a by-product of the acid decomposition, was driven off by distilling the reaction mixture in an nitrogen atmosphere(the amount of carbon disulfide recovered: 13.8 g). The remaining reaction mixture was then cooled to 10° C. and the resultant precipitate of crystalline potassium chloride was filtered off. The precipitate was then washed with 35% hydrochloric acid and the resulting washing was combined with the filtrate. A high-speed liquid chromatographic analysis on the resultant mixture of the washing and filtrate gave 88 mole % as the yield of DL-cystein based on β-chloroalanine.

To the mixture of the washing and filtrate, was added 17.6 g of p-toluenesulfonic acid hydrate, followed by its cooling to 5° C. or below. After stirring for 30 minutes, the resulting deposit of DL-cystein p-toluenesulfonate was collected through filtration and washed with a small amount of cold water. It was then dried to give 23.5 g of DL-cystein p-toluene sulfonate.

The DL-cystein p-toluene sulfonate was then taken up in 230 ml of methanol. By adding 8.1 g of triethylamine to the methanol solution and stirring same, 8.7 g of DL-cystein was deposited(yield: 71.8 mole % based on β-chloroalanine).

EXAMPLE 3

The procedure of Example 2 was repeated except that 61.9 g of a 55 wt. % aqueous solution of potassium sodium trithiocarbonate was employed in place of potassium trithiocarbonate and the reaction was carried out at 50° C. After the removal of carbon disulfide, the reaction liquid contained DL-cystein formed therein (yield: 83.5 mole % based on β-chloroalanine).

EXAMPLE 4

The procedure of Example 2 was followed except for the employment of 96.2 g of a 30 wt. % aqueous solution of ammonium trithiocarbonate in lieu of potassium trithiocarbonate. In the remaining reaction solution after removal of carbon disulfide, DL-cystein was formed with a yield of 78 mole % based on β-chloroalanine.

EXAMPLE 5

In 10 ml of water, 12.35 g of β-chloroalanine was dispersed. Then, 64.3 g of a 58 wt. % aqueous solution of potassium trithiocarbonate was charged dropwise in the course of approximately ten (10) minutes into the above aqueous dispersion system at 15°–20° C. while stirring the latter. They were then allowed to undergo a reaction at the same temperature for 5 hours. Thereafter, 14.6 g of hydrogen chloride gas was blown into the reaction mixture while maintaining the reaction mixture at 10°–20° C., thereby acidifying the reaction mixture. The resultant reaction mixture was stirred for one hour at the same temperature. Carbon disulfide, which occurred as a by-product due to the acid decomposition, was driven off through distillation(the amount of carbon disulfide recovered: 12.4 g), followed by cooling the remaining reaction mixture to 10° C. The resulting deposit of potassium chloride was filtered off and then washed with 35% HCL.

The thus-obtained washing and filtrate were combined and then subjected to an analysis by high-speed liquid chromatography. As a result, it was found that the yield of DL-cystein was 85.7 mole % based on β-chloroalanine.

We claim:

1. A process for producing DL-cystein, which process comprises reacting a β-halogenoalanine with a trithiocarbonate and then subjecting the resulting mono(aminocarboxyethyl) ester of trithiocarbonate to acid decomposition.

2. The process according to claim 1, wherein the β-halogenoalanine is β-chloroalanine or β-bromoalanine.

3. The process according to claim 1, wherein the trithiocarbonate is the alkali metal, alkaline earth metal or ammonium salt of trithiocarbonic acid.

4. The process according to claim 1, wherein the trithiocarbonate is used in an amount of 1–10 moles per mole of the β-halogenoalanine.

5. The process according to claim 1, wherein the β-halogenoaline is reacted with the trithiocarbonate at −20° C. to +100° C.

6. The process according to claim 1, wherein the acid decomposition is carried out using a mineral acid.

7. The process according to claim 1, wherein the acid decomposition is carried out at 0° C. to +80° C.

* * * * *